United States Patent [19]

Urbach et al.

[11] Patent Number: 4,857,520

[45] Date of Patent: Aug. 15, 1989

[54] FUSED AZEPINONE AND AZOCINONE DERIVATIVES, PROCESSES FOR THEIR PREPARATION, AGENTS CONTAINING THEM AND THEIR USE, AND INTERMEDIATES IN THEIR PREPARATION

[75] Inventors: Hansjörg Urbach, Kronberg/Taunus; Rainer Henning, Hattersheim am Main; Bernward Schölkens, Kelkheim; Reinhard Becker, Wiesbaden, all of Fed. Rep. of Germany

[73] Assignee: Hoechst Aktiengesellschaft, Frankfurt, Fed. Rep. of Germany

[21] Appl. No.: 155,595

[22] Filed: Feb. 12, 1988

[30] Foreign Application Priority Data

Feb. 14, 1987 [DE] Fed. Rep. of Germany ....... 3704661

[51] Int. Cl.$^4$ .................. A61K 31/555; C07D 223/10; C07D 225/04
[52] U.S. Cl. .................................... 514/183; 514/213; 540/461; 540/523
[58] Field of Search ................ 540/461, 523; 514/213, 514/183

[56] References Cited

U.S. PATENT DOCUMENTS 3,354,146 11/1967 Schnider et al. .................... 540/461
4,470,988 9/1984 Watthey .............................. 540/461

FOREIGN PATENT DOCUMENTS 0072352 2/1983 European Pat. Off. .
3426720 1/1986 Fed. Rep. of Germany .
2103614 2/1983 United Kingdom .

Primary Examiner—Robert T. Bond
Attorney, Agent, or Firm—Finnegan, Henderson, Farabow, Garrett, & Dunner

[57] ABSTRACT

The invention relates to compounds of the formula I

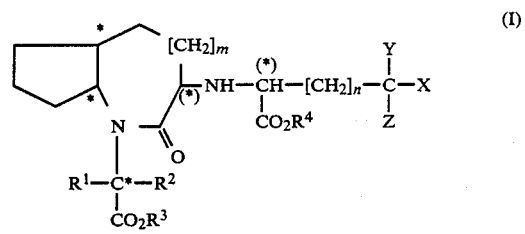

in which m denotes 1 or 2 and n denotes, 0, 1 or 2; $R^1$ and $R^2$ denote identical or different radicals from the series comprising hydrogen, optionally substituted alkyl, alkenyl, cycloalkyl, cycloalkenyl, cycloalkylalkyl, partly hydrogenated aryl and optionally substituted aralkyl; $R^3$ and $R^4$ denote identical or different radicals from the series comprising hydrogen, alkyl, alkenyl and optionally substituted aralkyl; Y denotes hydrogen or hydroxyl and Z denotes hydrogen, or Y and Z together denote oxo, and X denotes optionally substituted alkyl, alkenyl, cycloalkyl, optionally substituted 4-piperidinyl, optionally substituted aryl or indolyl, processes for their preparation, medicaments containing these compounds and their use, and to intermediates in their preparation.

10 Claims, No Drawings

FUSED AZEPINONE AND AZOCINONE DERIVATIVES, PROCESSES FOR THEIR PREPARATION, AGENTS CONTAINING THEM AND THEIR USE, AND INTERMEDIATES IN THEIR PREPARATION

Fused azepinone and azocinone derivatives, processes for their preparation, agents containing them and their use, and intermediates in their preparation.

Benzazepin-2-ones are known from European Patent A-72,352 and benzothiazepinone and benzothiazocinone derivatives are known from German Patent A1-3,426,720. Processes for their preparation and their use as inhibitors of angiotensin converting enzyme (ACE) are described.

The present invention is based on the fact that certain novel derivatives of azepinone and of azocinone have a potent inhibiting effect on angiotensin converting enzyme. This property makes these compounds particularly valuable for use on mammals—preferably on humans—in the treatment or prophylaxis of diseases which react to ACE inhibition, such as cardiovascular disorders (for example hypertension), cardiac conditions (for example cardiac insufficiency) and glaucoma.

The invention relates to compounds of the formula I

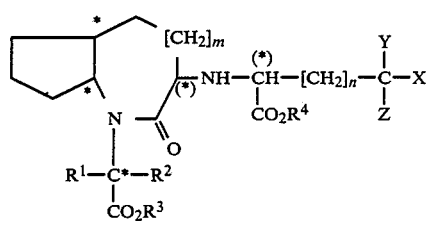

in which
n is 0, 1 or 2
m = 1 or 2 and
$R^1$ and $R^2$ are identical or different and denote hydrogen, $(C_1-C_6)$-alkyl, which can optionally be monosubstituted by hydroxyl, mercapto, $(C_1-C_2)$-alkoxy, $(C_1-C_2)$-alkylmercapto, carboxyl, $(C_1-C_2)$-alkoxycarbonyl, 3-indolyl, imidazolyl, carbamoyl, amino or guanidino, $(C_2-C_6)$-alkenyl, $(C_3-C_9)$-cycloalkyl, $(C_3-C_9)$-cycloalkenyl, $(C_3-C_7)$-cycloalkyl-$(C_1-C_4)$-alkyl, $(C_6-C_{12})$-aryl, partly hydrogenated $(C_6-C_{12})$-aryl or $(C_6-C_{12})$-aryl($C_1-C_4$)-alkyl, which can carry a hydroxyl group in the aryl part,
$R^3$ and $R^4$ are identical or different and denote hydrogen, $(C_1-C_6)$-alkyl, $(C_2-C_6)$-alkenyl or $(C_6-C_{12})$-aryl($C_1-C_4$)-alkyl, which can be monosubstituted in the aryl part by methoxy or nitro,
Y denotes hydrogen or hydroxyl,
Z denotes hydrogen or
Y and Z together denote oxygen, and
X represents $(C_1-C_6)$-alkyl, which can be substituted by amino, acylamino, $(C_1-C_4)$-alkylamino and/or di-$(C_1-C_4)$-alkylamino, $(C_2-C_6)$-alkenyl, $(C_5-C_9)$-cycloalkyl,

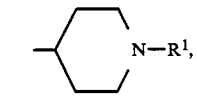

$(C_6-C_{12})$-aryl, which can be mono-, di- or trisubstituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or indol-3-yl, and in the abovementioned radicals, free hydroxyl, mercapto, carboxyl, amino or guanidino $R^1$, $R^2$ and X are optionally protected by protective groups customary in peptide chemistry,
and physiologically acceptable salts thereof.

Preferred compounds of the formula I are those in which
m is 1 and
n is 1,
$R^1$ is hydrogen, $(C_1-C_3)$-alkyl, $(C_3-C_6)$-cycloalkyl, $(C_3-C_6)$-cycloalkyl-$(C_1-C_2)$-alkyl or allyl,
$R^2$ is hydrogen, $(C_1-C_3)$-alkyl, $(C_3-C_6)$-cycloalkyl, $(C_3-C_6)$-cycloalkyl-$(C_1-C_2)$-alkyl or allyl,
$R^3$ is hydrogen, $(C_1-C_4)$-alkyl, benzyl or 4-methoxybenzyl,
$R^4$ is hydrogen, $(C_1-C_4)$-alkyl, benzyl or 4-methoxybenzyl,
X is phenyl or phenyl which is mono- or disubstituted by fluorine and/or chlorine, methyl, cyclohexyl or aminoethyl,
Y denotes hydrogen or hydroxyl, and
Z denotes hydrogen, or
Y and Z together represent oxygen,
and in particular compounds of the formula I in which
m=1,
n=1,
$R^1$, and $R^2$ and $R^3$ each denote hydrogen,
$R^4$=hydrogen or ethyl,
Y and Z each denote hydrogen and
X denotes phenyl.

Particularly preferred compounds which may be mentioned are:
(5a-S,8a-S)-1-carboxymethyl-3-(S)-[1-(S)-ethoxycarbonyl-3-phenyl-propylamino]-2-oxo-perhydrocyclopent[b]azepine
(5a-S,8a-R)-1-carboxymethyl-3-(S)-[1-(S)-ethoxycarbonyl-3-phenyl-propylamino]-2-oxo-perhydrocyclopent[b]azepine
(5a-R,8a-S)-1-carboxymethyl-3-(S)-[1-(S)-ethoxycarbonyl-3-phenyl-propylamino]-2-oxo-perhydrocyclopent[b]azepine
(5a-R,8a-R)-1-carboxymethyl-3-(S)-[1-(S)-ethoxycarbonyl-3-phenyl-propylamino]-2-oxo-perhydrocyclopent[b]azepine
(5a-S,8a-S)-1-carboxymethyl-3-(S)-[1-(S)-carboxy-3-phenyl-propylamino]-2-oxo-perhydrocyclopent[b]azepine
(5a-S,8a-R)-1-carboxymethyl-3-(S)-[1-(S)-carboxy-3-phenyl-propylamino]-2-oxo-perhydrocyclopent[b]azepine
(5a-R,8a-S)-1-carboxymethyl-3-(S)-[1-(S)-carboxy-3-phenyl-propylamino]-2-oxo-perhydrocyclopent[b]azepine
(5a-R,8a-R)-1-carboxymethyl-3-(S)-[1-(S)-carboxy-3-phenyl-propylamino]-2-oxo-perhydrocyclopent[b]azepine (5a-S,8a-S)-1-carboxymethyl-3-(S)-[1-(S)-ethoxycarbonyl-butylamino]-2-oxo-perhydrocyclopent[b]azepine
(5a-S,8a-R)-1-carboxymethyl-3-(S)-[1-(S)-ethoxycarbonyl-butylamino]-2-oxo-perhydrocyclopent[b]azepine
(5a-R,8a-S)-1-carboxymethyl-3-(S)-[1-(S)-ethoxycarbonyl-butylamino]-2-oxo-perhydrocyclopent[b]azepine
(5a-R,8a-R)-1-carboxymethyl-3-(S)-[1-(S)-ethoxycarbonyl-butylamino]-2-oxo-perhydrocyclopent[b]azepine
(5a-S,8a-S)-1-carboxymethyl-3-(S)-[1-(S)-Carboxybutylamino]-2-oxo-perhydrocyclopent[b]azepine
(5a-S,8a-R)-1-carboxymethyl-3-(S)-[1-(S)-carboxybutylamino]-2-oxo-perhydrocyclopent[b]azepine
(5a-R,8a-S)-1-carboxymethyl-3-(S)-[1-(S)-carboxybutylamino]-2-oxo-perhydrocyclopent[b]azepine
(5a-R,8a-R)-1-carboxymethyl-3-(S)-[1(S)-carboxybutylamino]-2-oxo-perhydrocyclopent[b]azepine
(5a-S,8a-S)-1-carboxymethyl-3-(S)-[1-(S)-ethoxycarbonyl-5-amino-pentylamino]-2-oxo-perhydrocyclopent[b]azepine
(5a-S,8a-R)-1-carboxymethyl-3-(S)-[1-(S)-ethoxycarbonyl-5-amino-pentylamino]-2-oxo-perhydrocyclopent[b]azepine
(5a-R,8a-S)-1-carboxymethyl-3-(S)-[1-(S)-ethoxycarbonyl-5-amino-pentylamino]-2-oxo-perhydrocyclopent[b]azepine
(5a-R,8a-R)-1-carboxymethyl-3-(S)-[1-(S)-ethoxycarbonyl-5-amino-pentylamino]-2-oxo-perhydrocyclopent[b]azepine
(5a-S,8a-S)-1-carboxymethyl-3-(S)-[1-(S)-carboxy-5-amino-pentylamino]-2-oxo-perhydrocyclopent[b]azepine
(5a-S,8a-R)-1-carboxymethyl-3-(S)-[1-(S)-carboxy-5-amino-pentylamino]-2-oxo-perhydrocyclopent[b]azepine
(5a-R,8a-S)-1-carboxymethyl-3-(S)-[1-(S)-carboxy-5-amino-pentylamino]-2-oxo-perhydrocyclopent[b]azepine
(5a-R,8a-R)-1-carboxymethyl-3-(S)-[1-(S)-carboxy-5-amino-pentylamino]-2-oxo-perhydrocyclopent[b]azepine
(6a-S,9a-S)-1-carboxymethyl-3-(S)-[1-(S)-ethoxycarbonyl-3-phenyl-propylamino]-2-oxo-perhydro-2H-cyclopent[b]azocine
(6a-S,9a-R)-1-carboxymethyl-3-(S)-[1-(S)-ethoxycarbonyl-3-phenyl-propylamino]-2-oxo-perhydro-2H-cyclopent[b]azocine
(6a-R,9a-S)-1-carboxymethyl-3-(S)-[1-(S)-ethoxycarbonyl-3-phenyl-propylamino]-2-oxo-perhydro-2H-cyclopent[b]azocine
(6a-R,9a-R)-1-carboxymethyl-3-(S)-[1-(S)-ethoxycarbonyl-3-phenyl-propylamino]-2-oxo-perhydro-2H-cyclopent[b]azocine
(6a-S,9a-S)-1-carboxymethyl-3-(S)-[1-(S)-carboxy-3-phenyl-propylamino]-2-oxo-perhydro-2H-cyclopent[b]azocine
(6a-S,9a-R)-1-carboxymethyl-3-(S)-[1-(S)-carboxy-3-phenyl-propylamino]-2-oxo-perhydro-2H-cyclopent[b]azocine
(6a-R,9a-S)-1-carboxymethyl-3-(S)-[1-(S)-carboxy-3-phenyl-propylamino]-2-oxo-perhydro-2H-cyclopent[b]azocine and
(6a-R,9a-R)-1-carboxymethyl-3-(S)-[1-(S)-carboxy-3-phenyl-propylamino]-2-oxo-perhydro-2H-cyclopent[b]azocine Particularly suitable salts are alkali metal and alkaline earth metal salts, salts with physiologically tolerated amines and salts with inorganic or organic acids, such as, for example, HCl, HBr, $H_2SO_4$, maleic acid, fumaric acid or tartaric acid.

Here and below, aryl is to be understood as optionally substituted phenyl, naphthyl or biphenylyl, in particular phenyl. The same applies to aralkyl. Acyl is understood, in particular, as ($C_1$–$C_6$)-alkanoyl, benzoyl, t-butoxycarbonyl (Boc) or benzyloxycarbonyl (Z). Alkyl can be straight-chain or branched.

Compounds of the formula I have chiral carbon atoms labeled with an asterisk. The invention relates to both the R- and the S-configuration on all the centers of asymmetry. The compounds of the formula I can therefore be in the form of optical isomers, diastereomers, racemates or mixtures thereof. However, compounds of the formula I in which the carbon atoms marked with an asterisk [(*)] have the S-configuration are preferred.

The invention furthermore relates to a process for the preparation of the compounds of the formula I, which comprises (a) reacting a compound of the formula II

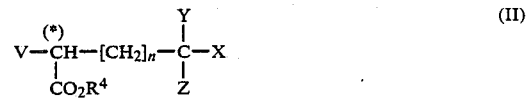

in which n, $R^4$, X, Y and Z are as defined above, but $R^4$ does not denote hydrogen, and V represents a leaving group which can be replaced nucleophilically, with a compound of the formula III

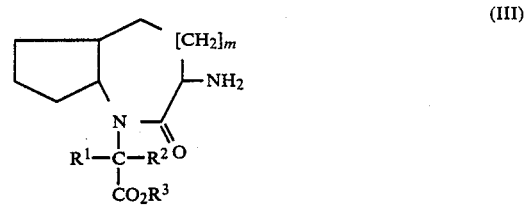

in which m, $R^1$, $R^2$ and $R^3$ are as defined above, but $R^3$ does not denote hydrogen, (b) reacting a compound of the formula III defined above with a compound of the formula IV

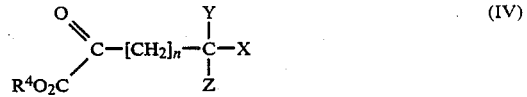

in which n, $R^4$ and X have the above meanings and Y and Z each denote hydrogen, in the presence of a reducing agent, (c) alkylating a compound of the formula V

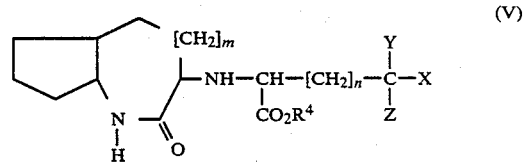

in which m, n, $R^4$, X, Y and Z are as defined above, with a compound of the formula VI

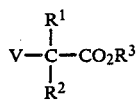
(VI)

in which $R^1$, $R^2$, $R^3$ and V are as defined above under (a), (d) reacting a compound of the formula VII

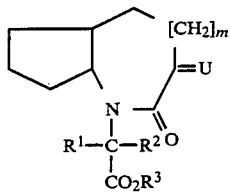
(VII)

in which m, $R^1$, $R^2$ and $R^3$ have the meanings defined above under (a) and U denotes an oxo group, or denotes hydrogen together with a group V defined under (a), with an amine of the formula VIII

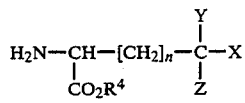
(VIII)

in which n, $R^4$ and X are as defined above under (a) and Y and Z denote hydrogen, the reaction being carried out in the presence of a reducing agent in the case where U=oxo, (e) cyclizing a compound of the formula IX

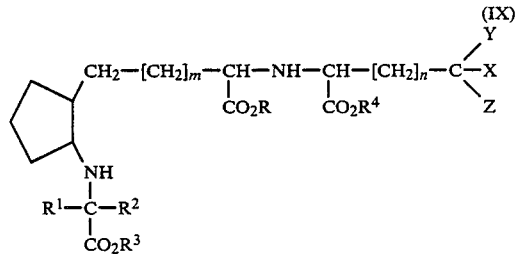
(IX)

in which m, n, $R^1$, $R^2$, $R^3$, $R^4$, X, Y and Z have the meanings given above under (a) and R denotes hydrogen or an ester group, or (f) to prepare compounds of the formula I in which Y and Z together denote oxygen, reacting a compound of the formula III defined under (a) with a compound of the formula X $$R^4O_2C-CH=CH-CO-X \qquad (X)$$

in which $R^4$ and X are as defined above in formula I, in a Michael reaction in a manner which is known per se (Organikum, 6th edition, (1967) 492), or reacting the abovementioned compound of the formula III with a compound of the formula XI $$OHC-CO_2R^4 \qquad (XI)$$

and a compound of the formula XII $$X-CO-CH_3 \qquad (XII)$$

in which $R^4$ and X have the meanings defined above in formula I, in a Mannich reaction in a manner which is known per se (Bull. Soc. Chim. France 1973, 620), and if Y and Z together denote oxygen (that is to say oxo), reducing this group to, if appropriate, Y=hydroxyl or hydrogen and Z=hydrogen, (i) if desired splitting off in a manner which is known per se any protective groups introduced temporarily for protection of functional groups, (ii) if appropriate esterifying carboxyl groups $CO_2R^3$ and/or $CO_2R^4(R^3,R^4=H)$ in a manner which is known per se to form compounds of the formula I ($R^3$ and/or $R^4 \neq H$), (iii) if appropriate splitting off the radicals $R^3$ and/or $R^4$ ($R^3,R^4 \neq H$) hydrolytically or hydrogenolytically to form the free carboxyl group(s), or reversing the sequence of these steps i–iii, and if appropriate converting the compounds of the formula I obtained in this manner into their physiologically acceptable salts.

In process variant (a), V denotes a leaving group which can be replaced nucleophilically ("nucleofugic" group), such as, for example, chlorine, bromine, iodine, mesyloxy, tosyloxy or trifluoromethylsulfonyloxy.

The reaction of a compound of the formula II with a compound of the formula III to prepare a compound of the formula I is carried out in a nucleophilic replacement reaction which is known per se. Compounds of the formula II in which Y and Z denote hydrogen and V denotes trifluoromethylsulfonyloxy have proved to be particularly suitable. If compounds of this type are reacted with compounds of the formula III in which m, $R^1$, $R^2$ and $R^3$ have the abovementioned meanings and an optically active compound of the formula II is employed, for example a compound of the formula II with the R configuration at the carbon atom labeled with an asterisk [(*)], the corresponding optically pure S-configurated derivatives of the formula I are obtained by Walden inversion. The reaction can preferably be carried out in an aprotic polar or non-polar solvent, such as, for example, methylene chloride, chloroform, toluene, dimethylformamide, dimethoxyethane, dimethylsulfoxide, carbon tetrachloride, ethyl acetate, hexane, ether, tetrahydrofuran or hexamethylphosphoric acid triamide, in the temperature range between −80° and +150° C., preferably between −20° C. and the boiling point of the reaction mixture. In order to trap the compound HV formed, such as, for example, trifluoromethanesulfonic acid, the reaction is advantageously carried out in the presence of preferably at least one equivalent of a base which cannot react with the compounds of the formula I or II or III. Tertiary amines, such as triethylamine or pyridine, have proved to be advantageous. The amino acid derivatives formed can also be used as acid-trapping agents. Inorganic bases, such as, for example, $Na_2CO_3$, $K_2CO_3$, $NaHCO_3$ or, in the case of the triflate, also $Na_2SO_4$, are also suitable.

The process in variant (b) corresponds to the procedure described in J. Amer. Chem. Soc. 93 (1971) 2897. The compounds of the formulae III and IV are reacted with one another in the presence of a reducing agent, such as complex metal hydrides (for example sodium cyanoborohydride or sodium borohydride) or hydrogen and metal catalysts (for example Raney nickel, Pd or Pt) in an inert solvent at a temperature between −20° and 150° C.

The reaction of compounds of the formula V with compounds of the formula VI in process variant (c) is carried out by deprotonating the lactam V with a strong base, such as, for example, sodium hydride or sodium amide, and then further reacting the product in a manner which is known per se in an aprotic polar or nonpolar solvent, such as dimethylformamide, dimethoxyethane or methylene chloride, at between −20° C. and 150° C.

Reducing agents which can be used for process variant (d) are described, for example, under (b). If U represents H+V, the reaction is carried out, if appropriate, in the presence of an organic or inorganic base, such as triethylamine or KOH.

In process variant (e), the radical R represents hydrogen or an ester group, ($C_1$–$C_6$)-alkyl esters or ($C_7$ to $C_9$)-aralkyl esters (such as benzyl esters) being preferred. The cyclization is carried out in a manner which is known per se, for example by the methods such as are customary in peptide chemistry (such as the carbodiimide method, Peptides, volume I, Academic Press, London, New York 1965, page 108), or under acid or basic catalysis in a polar solvent, preferably an alcohol, at a temperature between about 10° C. and the boiling point of the reaction mixture.

If compounds of the formula I in which $R^3$ and/or $R^4$ are other than hydrogen are obtained in processes (a) to (f), if appropriate these can be subjected to hydrogenolysis or acid or basic hydrolysis in order to obtain compounds of the formula I in which $R^3$ and/or $R^4$ are hydrogen.

Compounds of the formula I where Y=hydroxyl and Z=hydrogen can also be obtained, for example, by reduction of a compound I where Y and Z together are oxygen in accordance with the above procedures. This reduction can be carried out with a reducing agent, such as sodium borohydride and other complex boronates, or for example, borane-amine complexes.

If appropriate, compounds of the formula I in which $R^3$ and/or $R^4$ represent hydrogen can be converted into their esters by methods which are known per se. An important method is direct esterification of free acids (alcoholysis of carboxylic acids).

As a result of the low carbonyl activity, carboxylic acids in general react only slowly with alcohols. By adding strong acids (sulfuric acid, anhydrous hydrogen chloride, sulfonic acids or acid ion exchangers), the esterification can be accelerated considerably.

The esterification equilibrium can be shifted to the right by using the alcohol in a 5- to 10-fold excess or by continuously removing water from the reaction mixture.

In the simplest case, the water formed is bonded by the catalyst acid added (sulfuric acid or hydrochloric acid). Removal of the water by azeotropic distillation is also advantageous. The choice of entraining agent depends on the boiling point of the lowest-boiling organic component. Chloroform or carbon tetrachloride can be used to prepare ethyl esters and propyl esters. Alcohols higher than butanol themselves form azeotropes with water, so that no further entraining agent has to be added.

In the so-called extractive esterification, the ester formed is dissolved selectively out of the reaction mixture by a solvent which dissolves only very little water. The method is suitable above all for the preparation of methyl esters, where azeotropic esterification with simple agents is not successful.

In contrast to direct esterification of the carboxylic acids, the esters of the tertiary alcohols and of phenols can also be prepared from the corresponding acid halides.

The following protective groups which are customary in peptide chemistry are suitable for protecting free functional groups in the radicals $R^1$, $R^2$, $R^3$, $R^4$ and X.

Phenolic OH groups are protected, for example, with acyl groups of the benzyloxycarbonyl type (such as Z or BrZ) or with O-alkyl groups (such as Bzl, Mob, Pic or $Bu^t$).

O-Alkyl groups, such as $Bu^t$ or Bzl, are used above all for protecting alcoholic OH groups.

Carboxyl-protective groups which are frequently used are the alkyl ester groups, such as OMe, OEt, OBzl, ONbzl, OMbzl, OPic, $OBu^t$ or OPac.

The amino group is advantageously protected with a protective group of the urethane type, such as, in particular, Boc or Z, and also Pyoc, Fmoc, Tcboc, Ddz, Bpoc, Z($NO_2$), Moc, Mboc, Iboc, Adoc or Adpoc.

The guanidino group can be protected, for example, by means of nitration or some of the abovementioned urethane protective groups.

Thiol is protected, for example, as thioether, S-acetal or unsymmetric disulfide.

Protective groups in peptide synthesis (abbreviations, introduction and splitting off of these groups) are described comprehensively in Kontakte Merck (Merck Contacts) 7/79, pages 14–22 and 1/80, pages 23–35 (in this context, see also Schröder, Lübke "The Peptides", volume 1, Academic Press New York, London 1965).

Compounds of the formula II to IX can be used as racemates, diastereomers or optically pure compounds. Diastereomers of the formula I can be separated from one another by, for example, crystallization or chromatography. If diastereomers are produced at all by the reactions described, these can be separated by crystallization or chromatography.

The invention also relates to compounds of the formula XIII

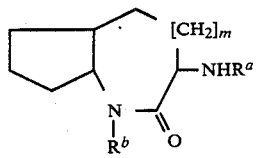

(XIII)

in which
m is as defined above,
(a) $R^a$ and $R^b$ each denote hydrogen,
(b) $R^a$ denotes hydrogen and $R^b$ represents a radical

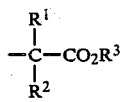

in which $R^1$, $R^2$ and $R^3$ are as defined above,
(c) $R^a$ represents a radical

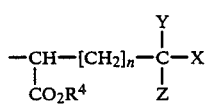

in which n, $R^4$, X, Y and Z are as defined above and $R^b$ denotes hydrogen, or (d) $R^a$ represents a radical

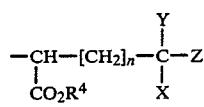

in which n, $R^4$, X, Y and Z are as defined above, and $R^b$ represents a radical

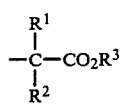

in which $R^1$, $R^2$ and $R^3$ are as defined above, and to a process for the preparation of these compounds, which comprises (a) cyclizing compounds of the formula XIV

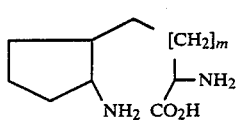 (XIV)

in which m is as defined above, to give compounds of the formula XV ($\cong$ formula XIII where $R^a$ and $R^b$ are each hydrogen)

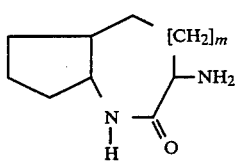 (XV)

in which m is as defined above, (b) reducing compounds of the formula XVI

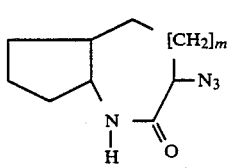 (XVI)

in which m is as defined above, to compounds of the formula XV defined above, (c) if appropriate alkylating compounds of the formula XV with compounds of the formula VI

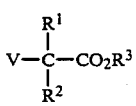 (VI)

in which V, $R^1$, $R^2$ and $R^3$ are defined as in the process for the preparation of compounds of the formula I under (c), to give compounds of the formula III ($\triangleq$ formula XIII with $R^a$=H, $R^b\neq$H), (d) if appropriate reacting compounds of the above formula XV with compounds of the formula II defined in the preparation process for compounds of the formula I under (a) to give compounds of the formula V ($\cong$ formula XIII where $R^a\neq$H, $R^b$=H), (e) reacting compounds of the above formula XV with a compound of the formula X $$R^4O_2C-CH=CH-CO-X \quad (X)$$

in which $R^4$ and X are as defined above in formula I, in a Michael reaction in a manner which is known per se, or reacting the abovementioned compound of the formula III with a compound of the formula XI $$OHC-CO_2R^4 \quad (XI)$$

and a compound of the formula XII $$X-CO-CH_3 \quad (XII)$$

in which $R^4$ and X have the meanings defined in claim 1 in formula I, in a Mannich reaction in a manner which is known per se, and if Y and Z together denote hydrogen, if appropriate reducing this group to Y=hydroxyl or hydrogen and Z=hydrogen, (f) or alkylating a compound of the formula XVI with compounds of the formula VI to give compounds of the formula XVII

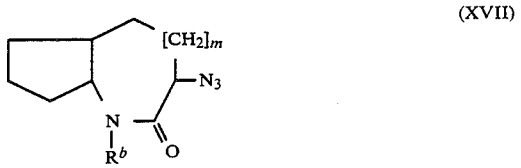 (XVII)

in which m and $R^b$ ($R^b\neq$H) are as defined above under (b) (page 14), and converting these compounds into compounds of the formula XIII ($R^a$=H, $R^b\neq$H) by catalytic hydrogenation with metal catalysts or by reaction with complex hydrides.

Compounds of the formula XIV as starting compounds for process variant (a) are prepared by reacting compounds of the formula XVIII

 (XVIII)

in which $X^1$ represents dialkylamino with 2 to 10 carbon atoms or represents a radical of the formula

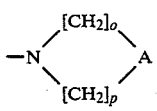

in which o and p denote an integer from 1 to 3, (o+p)$\geq$3 and A denotes $CH_2$, NH, N-($C_1$-$C_6$)-alkyl, O or S, with compounds of the formula XIX

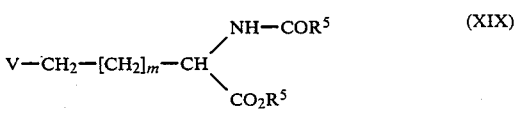 (XIX)

in which V and m have the abovementioned meaning, V preferably representing chlorine, bromine, iodine or tosyloxy, and $R^5$ denotes hydrogen or $(C_1-C_4)$-alkyl, in the presence of a base, such as, for example, a tertiary amine, in an organic aprotic polar or non-polar solvent at temperatures from $-20°$ C. to $150°$ C., preferably $20°$ C. to $150°$ C., and subsequently subjecting the product to mild acid hydrolysis (for example with aqueous mineral acids), to give compounds of the formula XX

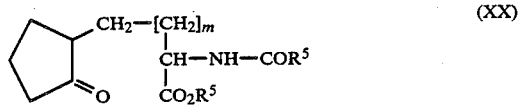

in which m and $R^5$ are as defined above.

After protection of the carboxyl and amino group under conditions such as are customary in amino acid or peptide chemistry, compounds of the formula XIX can be prepared from homoserine (m=1). A corresponding procedure is followed for preparation of the compounds of the formula XIX where m=2.

The compounds of the formula XX are converted in a manner which is known per se with hydroxylamine or salts into the oximes XXa, in which m and $R^5$ have the above meaning, which are in turn converted under reductive conditions into the amines of the formula XXb in which m and $R^5$ have the above meaning. The reduction can be carried out with hydrogen and a metal catalyst, such as, for example, Pt, Pt-on-charcoal, $PtO_2$, Pd, Pd-on-charcoal or Raney nickel, or with complex hydrides, such as, for example, sodium cyanoborohydride.

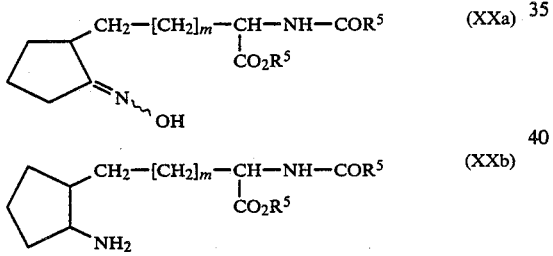

The compounds of the formula XX b are in the form of diastereomeric mixtures, which if appropriate can be separated by crystallization or chromatography.

The compounds of the formula XX b thus obtained are saponified under acid or alkaline conditions in a manner which is known per se to give compounds of the formula XIV, which can be obtained as corresponding salts depending on their hydrolysis conditions. The cyclization to give the compounds of the formula XV can be carried out under acid or alkaline conditions in a polar or apolar solvent between room temperature and the boiling point of the reaction mixture, preferably at elevated temperature, or under conditions which are customary in peptide chemistry for the formation of amide bonds. The reaction with a diamide, such as, for example, dicyclohexylcarbodiimide, proves to be particularly advantageous for cyclization of the compounds of the formula XIV, and the presence of hydroxybenzotriazole can accelerate the reaction. An aprotic polar or non-polar solvent can be taken as the solvent. Dimethylformamide, for example, proves to be particularly advantageous. The reaction temperature can be in the range from $-20°$ to $80°$ C. Cyclization can be achieved particularly advantageously with alkylphosphonic acid anhydrides or dialkylphosphinic acid anhydrides in an aprotic polar or non-polar solvent. n-Propanephosphonic acid anhydride or methyl ethyl phosphinic acid anhydride under the reaction conditions described in U.S. Pat. Nos. 4,331,592 and 4,426,325 have proved to be particularly suitable.

The reaction is carried out, for example, in a neutral or weakly alkaline medium. The easiest method is to adjust the pH of the medium by addition of aliphatic or cycloaliphatic tertiary bases, such as, for example, N-methylmorpholine, N-ethylmorpholine or trialkylamines with up to 6 carbon atoms per alkyl radical. If mixed aqueous systems are used, alkaline salts which act as buffer systems, such as, for example, those of carbonic acid or of phosphoric acid, can also be used instead of the organic base.

Azides of the formula XVI are obtained by halogenating compounds of the formula XXI

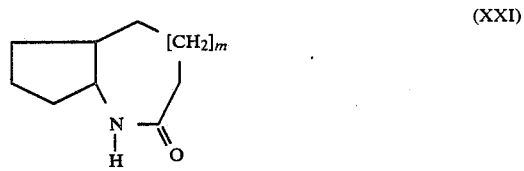

in which m has the abovementioned meaning, to give compounds of the formula XXII

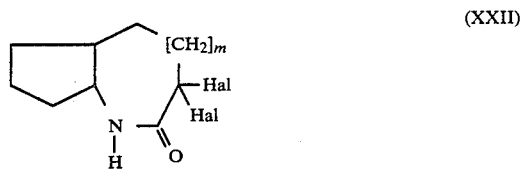

in which m is as defined above and Hal denotes halogen, preferably chlorine or bromine, and reducing these catalytically to give compounds of the formula XXIII

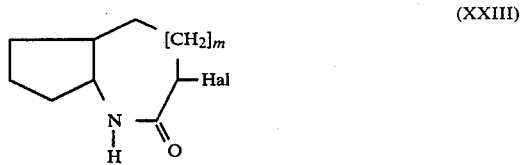

in which m and Hal have the above meaning.

Compounds of the formula XXI in which m is as defined above can be prepared, for example, by alkylation and condensation of the compounds of the formula XVIII or the alkali metal salts of the compounds of the formula XXIV (in which $R^5$ is as defined above, but $R^5 \neq H$), with
- ω-halogenobutyric acids or
- ω-halogenobutyric acid derivatives, such as, for example, 4-bromobutyryl bromide or
- alkyl 4-bromobutyrates, or the corresponding $C_5$-homologs, in a manner which is known per se.

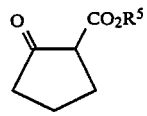 (XXIV)

Possible halogenating agents for compounds of the formula XXI are, for example, inorganic acid halides, such as PCl$_5$, SO$_2$Cl$_2$, POCl$_3$, SOCl$_2$ or PBr$_3$, or halogen, such as bromine or chlorine. It is advantageous to use PCl$_5$ or POCl$_3$ in combination with SO$_2$Cl$_2$ in an organic solvent. An imide halide is formed as an intermediate and further reacts with the halogenating agents mentioned and undergoes subsequent hydrolysis under basic conditions, preferably with aqueous alkali metal carbonate, to give a compound of the formula XXII.

The compounds of the formula XXII are subsequently reduced catalytically in a polar aprotic solvent, such as, for example, an alcohol, preferably ethanol, or a carboxylic acid, such as, for example, acetic acid, with the addition of an acid acceptor, such as, for example, sodium acetate or triethylamine, to give a compound of the formula XXIII in which Hal has the abovementioned meaning. Examples of possible catalysts are Raney nickel or palladium- or platinum-on-animal charcoal.

Compounds of the formula XXIII can also be prepared directly or as a mixture with compounds of the formula XXII by halogenation of the compounds of the formula XXI using smaller amounts of the abovementioned halogenating agents.

Compounds of the formula XXIII can also be obtained by reacting compounds of the formula XVIII with dihalogen acid derivatives of the formula XXV

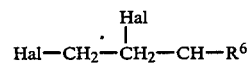 (XXV)

in which Hal denotes halogen, such as, for example, chlorine or bromine, and R$^6$ denotes a carboxylic acid function, such as, for example, a carboxyl, carbalkoxy, carboxylic acid halide or cyano group, in a condensation reaction.

The compounds of the formula XXIII are reacted with nucleophiles which replace the halogen by a group which liberates an amino group in further reaction steps. For example, compounds of the formula XXIII are reacted with an azide, preferably sodium azide, in a non-polar or polar solvent, such as, for example, dimethylsulfoxide, at temperatures between 0° C. and 100° C., preferably between 50° C. and 100° C. Azides of the abovementioned formula XXVI are obtained. The nucleophilic replacement takes place under Walden inversion.

The azides can be converted into the compounds of the formula XV by catalytic hydrogenation with metal catalysts or by reaction with complex hydrides. For example, the azide group is reduced with Raney nickel in an alcohol, such as, for example, ethanol, at room temperature with stirring to give the amino compound of the formula XV.

The compounds of the formulae XV, XVI, XXI, XXII and XXIII used as intermediates have several chiral centers. They can thus be in the form of diastereomers, which can be separated by crystallization or chromatographic methods. Diastereomers or diastereomeric mixtures and enantiomers or enantiomeric mixtures can be used.

The diastereomers of the compounds of the formulae XV, XVI, XXI, XXII and XXIII are described below, m and Hal being as defined above:

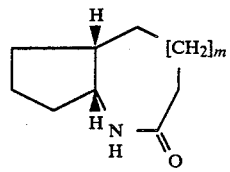 XXIa

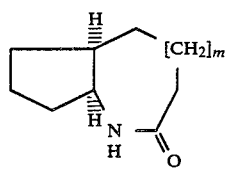 XXIb

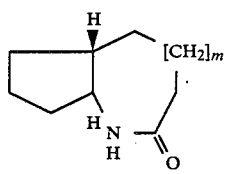 XXIc

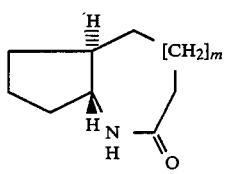 XXId

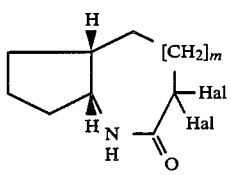 XXIIa

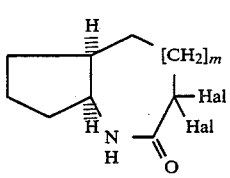 XXIIb

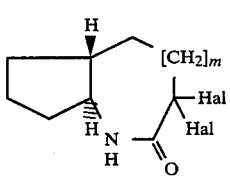 XXIIc

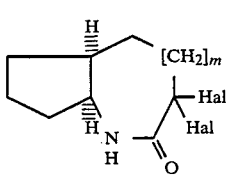 XXIId

-continued
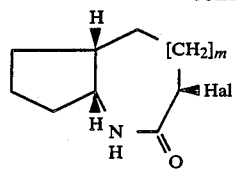 XXIIIa
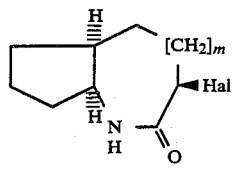 XXIIIb
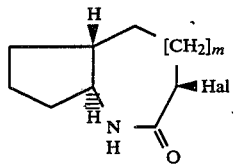 XXIIIc
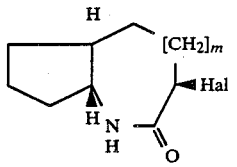 XXIIId
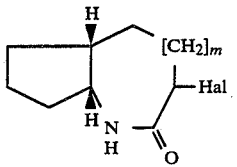 XXIIIe
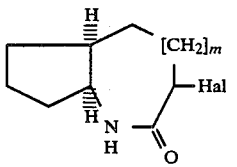 XXIIIf
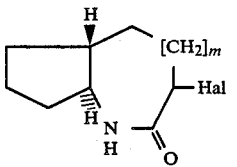 XXIIIg
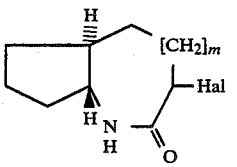 XXIIIh
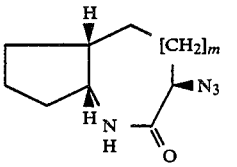 XVIa
-continued
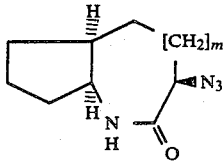 XVIb
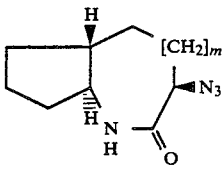 XVIc
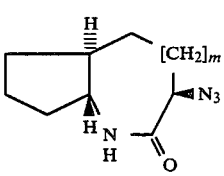 XVId
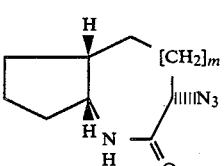 XVIe
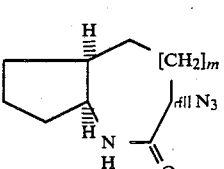 XVIf
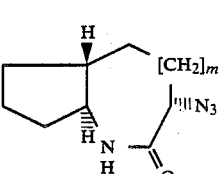 XVIg
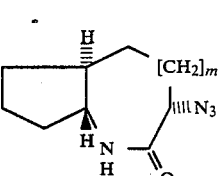 XVIh
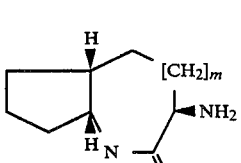 XVa
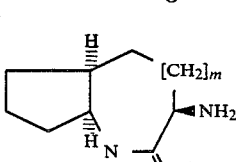 XVb

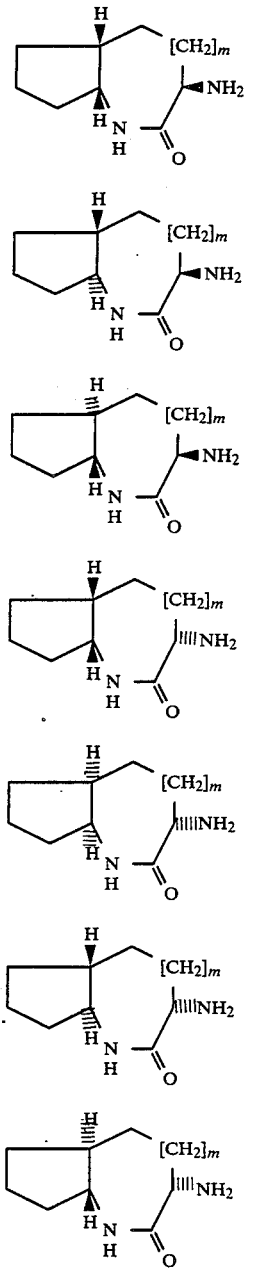

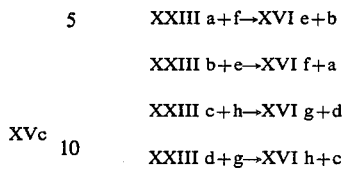

After halogenation of the compounds of the formula XXI, the compounds of the formula XXII are advantageously separated into the diastereomers XXII a+b (mirror images of the cis compound) and XXII c+d (mirror images of the trans compound). These diastereomers are advantageously employed separately in the subsequent reactions in order to save separation problems.

The compounds of the formula XXIII a+f (mirror images of the cis-exo compound) and the compounds of the formulae XXIII b+e (mirror images of the cis-endo compound) are obtained from the compounds of the formula XXII a+b by the procedures described above, and the compounds of the formula XXIII c+h and the compounds of the formula XXIII d+g are obtained from the compounds of the formula XXII c+d. Since the reaction of the compounds of the formula XXIII with NaN₃ takes place under Walden inversion, the following are obtained:

XXIII a+f→XVI e+b

XXIII b+e→XVI f+a

XXIII c+h→XVI g+d

XXIII d+g→XVI h+c

The compounds of the formula XV prepared by the above processes can easily be converted into compounds of the formula III by alkylation with compounds of the formula VI (process variant (c), page 18).

The reaction here is advantageously carried out in an aprotic non-polar or polar solvent in the presence of a strong base, which can be, for example, sodium hydride. Sodium hydride deprotonates the lactam nitrogen and the salt formed then reacts particularly advantageously with compounds of the formula VI in which V denotes halogen, in particular bromine, to give compounds of the formula III. The salt formation can be carried out in the temperature range between −30° and +80° C., whilst the subsequent reaction can be carried out at 0° to 150° C.

Under these conditions, compounds of the formula XV can also easily be converted into compounds of the formula XVII ($R^b \neq H$). The compounds of the formula XVII ($R^b \neq H$) can then be reduced by catalytic hydrogenation with metal catalysts or reaction with complex hydrides to give compounds of the formula III.

The process conditions for the preparation of the compounds of the formula V according to variant (d) are largely similar to those of variant (a) in the preparation of compounds of the formula I.

The invention furthermore relates to the use of compounds of the formula I as medicines in the treatment or prophylaxis of, in particular, cardiovascular disorders.

The invention also relates to pharmaceutical agents containing a compound of the formula I and a physiologically acceptable excipient and to a process for the preparation of these agents, which comprises bringing a compound of the formula I into a suitable presentation form together with a physiologically acceptable excipient and if appropriate other auxiliaries.

The compounds of the formula I according to the invention are inhibitors of angiotensin converting enzyme (ACE), which catalyzes the conversion of angiotensin I into angiotensin II, which has a pressor action. After intraduodenal administration to anesthetized rats, a powerful inhibiting action on the pressor reaction caused by intravenous administration of 310 ng of angiotensin I is observed.

The compounds of the formula I and its salts have a long-lasting intensely antihypertensive action. They can be used for combating hypertension of various origins or heart diseases, for example cardiac insufficiency. They can also be combined with other antihypertensives, for example $Ca^{2+}$-antagonists, vasodilating or diuretic compounds. Typical representatives of these classes of action are described, for example, in Erhardt-Ruschig, Arzneimittel (Drugs), 2nd edition, Weinheim 1972. The compounds can be used intravenously, subcutaneously or perorally.

The dosage for peroral administration is 0.01–10 mg/kg/day, in particular 0.07–3.0 mg/kg/day. In severe cases, it can also be increased, since no toxic effects have yet been observed. It is also possible to reduce the dose, and this is especially appropriate if diuretics or calcium antagonists are administered simultaneously.

The compounds according to the invention can be administered orally or parenterally in an appropriate pharmaceutical formulation. For an oral use form, the active compounds are mixed with the additives customary for this purpose, such as excipients, stabilizers or inert diluents, and the mixtures are brought by customary methods into a suitable presentation form, such as tablets, coated tablets, pushfit capsules, aqueous, alcoholic or oily suspensions or aqueous, alcoholic or oily solutions. Possible inert excipients are, for example, gum arabic, magnesium carbonate, potassium phosphate, lactose, glucose or starch, in particular maize starch. They can be formulated either as dry or as moist granules. Possible oily excipients or solvents are, for example, vegetable or animal oils, such as sunflower oil or cod-liver oil.

For subcutaneous or intravenous administration, the active compounds or physiologically tolerated salts thereof are dissolved, suspended or emulsified, if desired with the customary substances for this, such as solubilizing agents or other auxiliaries.

Possible solubilizing agents for the novel active compounds and salts thereof are, for example: water, propanediol or glycerol, and in addition also sugar solutions, such as glucose solutions or mannitol solutions, or a mixture of the solvents mentioned.

When administered systemically, and in particular when applied topically, the compounds according to the invention can be used for the treatment of glaucoma.

The following examples illustrate the invention.

EXAMPLE I (3-S,5a-S,8a-S)-1-carboxymethyl-3-[1-(S)-ethoxycarbonyl-3-phenylpropylamino]-2-oxo-perhydrocyclopent[b]azepine (cis-exo)

(1) 4-[2-Oxo-cyclopentyl]-butyric acid 28 g of sodium hydride (55% strength) are suspended in 400 ml of dry dimethylformamide, and 100 g of ethyl cyclopentanone-2-carboxylate in 400 ml of dry dimethylformamide are added dropwise, while cooling with ice. When the evolution of hydrogen has ended, ethyl 4-bromobutyrate is added dropwise. After 14 hours under reflux, the solution is evaporated on a rotary evaporator, the residue is taken up in water and the mixture is extracted with methylene chloride. After drying, the methylene chloride is evaporated off and the residue is distilled.

Yield: 144 g of ethyl 4-[1-ethoxycarbonyl-2-oxo-cyclopentyl]-butyrate, boiling point: 139°–145° C. (0.09 mm Hg).

136 g of the compound obtained above are dissolved in 312 ml of glacial acetic acid; 77 ml of concentrated aqueous HCl are added, and the mixture is refluxed for 16 hours. After customary working up, the residue is distilled.

Yield: 52 g, boiling point: 142°–158° C./0.008 mm Hg

(2) Ethyl 4-(2-oxo-cyclopentyl)-butyrate 17 g from Example I (1) are left to stand in 170 ml of ethanolic HCl for 14 hours. After working up, the residue is distilled.

Yield: 15 g, boiling point: 98°–104° C./0.1 mm Hg

(3) Ethyl 4-(2-hydroximino-cyclopentyl)-butyrate 13 g from Example I (2) are added dropwise to a hot solution, at 60° C., of 6.8 g of hydroxylamine hydrochloride and 6.5 g of sodium acetate in 35 ml of water. After the mixture has been stirred for 80 minutes and cooled, it is extracted with methylene chloride. The residue which remains after the evaporation is separated over silica gel with cyclohexane/ethyl acetate 7:3 as the mobile phase.

Yield: 12 g, $R_f$: 0.3 (silica gel; $CH_2Cl_2/CH_3OH$ 95:5)

(4) Ethyl 4-(2-amino-cyclopentyl)-butyrate 12.8 g of oxime from Example I (3) are dissolved in 128 ml of glacial acetic acid, 1.3 g of platinum oxide are added and the mixture is hydrogenated in an autoclave under a hydrogen pressure of 10 atmospheres for 8 hours. After the catalyst has been filtered off with suction, the filtrate is concentrated in vacuo, the residue is taken up in methylene chloride and the mixture is extracted with 2N aqueous HCl. The HCl phase is rendered basic with sodium hydroxide solution and extracted with methylene chloride.

Yield: 3.4 g

(5) 4-(2-Amino-cyclopentyl)-butyric acid 3.4 g of amine ester from Example I (4) are dissolved in 20 ml of 6N aqueous HCl and the solution is refluxed for 5 hours. After cooling, it is extracted with $CH_2Cl_2$ and the HCl phase is evaporated on a rotary evaporator. The residue is evaporated several times with toluene, and ethyl acetate/isopropanol is added.

Yield: 2.7 g, melting point: 174°–177° C. (HCl salt)

(6) 2-Oxo-perhydrocyclopent[b]azepine 4.1 g of amino acid hydrochloride from Example I (5) are suspended in 40 ml of methylene chloride, 12.8 ml of N-ethylmorpholine are added, while cooling with ice, and 12.8 ml of 50% strength n-propanephosphonic acid anhydride in methylene chloride are added dropwise at 0° C. The solution is left to stand at room temperature for 14 hours. It is then diluted with 200 ml of $CH_2Cl_2$ and extracted with water, 2N HCl and saturated NaHCO$_3$ solution. The $CH_2Cl_2$ phase is dried and evaporated.

Yield: 2.6 g, melting point: 131°–133° C., recrystallization from petroleum ether, melting point 133°–135° C.

(7) 2-Oxo-3,3-dichloro-perhydrocyclopent[b]azepine 1.0 g of lactam from Example I (6) are dissolved in 28 ml of xylene, 4.1 g of PCl$_5$ are added under N$_2$ and the mixture is then heated at 50° C. for 30 minutes and then at 90° C. for a further 30 minutes. After cooling, it is concentrated in vacuo. Saturated aqueous Na$_2$CO$_3$ solution is added to the residue and the mixture is then diluted with H$_2$O. It is extracted with $CH_2Cl_2$ and the methylene chloride phase is dried and concentrated. The residue is stirred with diisopropyl ether.

Yield: 1.0 g, melting point: 135°–140° C.

This 1 g is a mixture which is separated over silica gel with cyclohexane/ethyl acetate 4:1. The product eluted first is the cis compound (5a-RS,8aRS)-2-oxo-3,3-dichloro-perhydrocyclopent[b]azepine (A), melting point: 132°–135° C.;

$^1$H-NMR (CDCl$_3$): H$_{8a}$: 4.08 ppm (ddd, $\cong \sim 2.3 + 5.5 + 5.5$ Hz).

The compound eluted next is the trans product (5a-RS,8a-SR)-2-oxo-3,3-dichloro-perhydrocyclopent[b]azepine (B),
melting point: 194°–196° C.;
$^1$H-NMR (CDCl$_3$): H$_{8a}$: 3.6 ppm (ddd, J~7.5+10+10 Hz)
(A) and (B) are racemates.

(8)
(5a-RS,8a-RS)-2-Oxo-3-chloro-perhydrocyclopent[b]azepine (cis)

100 mg of the cis compound (A) from Example I (7) are dissolved in 10 ml of glacial acetic acid containing 55 mg of anhydrous sodium acetate, 10 mg of Pd/C (5% strength) are added and the mixture is hydrogenated at room temperature under normal pressure until 1 molar equivalent of hydrogen has been taken up. The catalyst is filtered off, the solution is concentrated, aqueous NaHCO$_3$ solution is added, the mixture is extracted with CH$_2$Cl$_2$ and the CH$_2$Cl$_2$ phase is dried and concentrated. The residue consists of 2 diastereomeric monochloro compounds, which are separated over silica gel with cyclohexane/ethyl acetate 1:1.

The product eluted first is the "cis-exo" compound (A) (3-RS,5a-RS,8a-RS)-2-Oxo-3-chloro-perhydrocyclopent[b]azepine
Melting point: 112°–113° C.
$^1$H-NMR (CDCl$_3$): H$_3$: 4.25 ppm (multiplet), H$_{8a}$: 4.52 ppm (multiplet)

The compound eluted next is the "cis-endo" compound (B) (3-SR,5a-RS,8a-RS)-2-oxo-3-chloro-perhydrocyclopent[b]azepine
Melting point: 130°–131° C.
$^1$H-NMR (CDCl$_3$): H$_3$: 3.92 ppm (multiplet), H$_{8a}$: 4.71 ppm (dd)

(9)
(3-SR,5a-SR,8a-RS)-2-Oxo-3-chloro-perhydrocyclopent[b]azepine (trans)

100 mg of the trans compound (B) from Example I (7) are hydrogenated as described in Example I (8). A monochloro compound is formed.
Melting point: 180°–183° C.
$^1$H-NMR (CDCl$_3$): H$_3$: 3.3 ppm (multiplet), H$_{8a}$: 4.65 ppm (dd)

The relative configuration was determined by $^1$H-NMR-NOE (Nuclear Overhauser Effect) measurements.

(10)
(3-SR,5a-RS,8a-RS)-2-Oxo-3-azido-perhydrocyclopent[b]azepine (cis-endo)

100 mg of the "cis-exo" compound (A) from Example I (8) are dissolved in 2 ml of dimethylsulfoxide, and 41.5 mg of sodium azide are added. The mixture is heated at 80° C. for 6 hours. After cooling, water is added and the mixture is then extracted with methylene chloride. After drying, the CH$_2$Cl$_2$ phase is concentrated. The residue is stirred with diisopropyl ether.
Yield: 77 mg, melting point 108°–110° C.
$^1$H-NMR (CDCl$_3$): H$_3$: 3.85 ppm (multiplet) H$_{8a}$: 4.02 ppm (dd)

(11)
(3-RS,5a-RS,8a-RS)-2-Oxo-3-azido-perhydrocyclopent[b]azepine (cis-exo)

100 mg of the "cis-endo" compound (B) from Example I (8) are reacted as described in Example I (10).
Yield: 81 mg melting point: 68°–69° C.
$^1$H-NMR (CDCl$_3$): H$_3$: 4.12 (multiplet) H$_{8a}$: 4.27 (multiplet: after H/D exchange dd)

(12)
(3-RS,5a-SR,8a-RS)-2-Oxo-3-azido-perhydrocyclopent[b]azepine (trans)

1.5 g of the trans compound from Example I (9) are reacted as described in Example I (10).
Yield: 1.4 g, melting point: 116°–118° C.
$^1$H-NMR (CDCl$_3$): H$_3$: 3.65 ppm (multiplet), H$_{8a}$: 4.38 ppm (doublet)

(13)
(3-SR,5a-RS,8a-RS)-1-Tert-butoxycarbonylmethyl-2-oxo-3-azido-perhydrocyclopent[b]azepine (cis-endo)

122 mg of sodium hydride suspension (55–60% strength) are washed with n-hexane and the sodium hydride is suspended in 27 ml of dry dimethylformamide. 900 mg of the "cis-endo" azide compound from Example I (10) are then added dropwise at 0° C. and the mixture is subsequently stirred for 45 minutes. 994 mg of tert.-butyl bromoacetate in dry dimethylformamide are then added dropwise at 0° C.; the mixture is allowed to come to room temperature and is subsequently stirred overnight. The dimethylformamide is evaporated off in a rotary evaporator and the residue is dispersed in 50 ml of methylene chloride. The aqueous phase is extracted again with methylene chloride. After drying, the methylene chloride phases are concentrated and the residue is stirred with petroleum ether.
Yield: 0.65 g, melting point: 102°–105° C.
$^1$H-NMR (CDCl$_3$): 1.45 ppm (singlet, 9H), 4.07 ppm (multiplet), 4.16 ppm (quartet),

(14)
(3-RS,5a-RS,8a-RS)-1-Tert.butoxycarbonylmethyl-2-oxo-3-azido-perhydrocyclopent[b]azepine (cis-exo)

900 mg of the "cis-exo" azide compound from Example I (11) are reacted analogously to Example I (13)
Melting point: 75°–77° C.
$^1$H-NMR(CDCl$_3$): 1.45 ppm (singlet, 9H), 3.74 ppm (multiplet, 1H), 3.78 ppm (doublet, 1H), 3.95 ppm (multiplet, 1H), 4.45 ppm (doublet, 1H)

(15)
(3-RS,5a-SR,8a-RS)-1-Tert.-butoxycarbonylmethyl-2-oxo-3-azido-perhydrocyclopent[b]azepine (trans)

600 mg of the trans azide compound from Example I (12) are reacted analogously to Example I (14).
Yield: 0.6 g of oil
$^1$H-NMR(CDCl$_3$): 1.45 ppm (singlet, 9H), 3.98 ppm (doublet, 1H), 4.08 ppm (multiplet, 1H), 4.22 ppm (doublet, 1H), 4.56 ppm (dd, 1H),

(16)
(3-SR,5a-RS,8a-RS)-1-Tert.-butoxycarbonylmethyl-2-oxo-3-amino-perhydrocyclopent[b]azepine (cis-endo)

600 mg of azide compound from Example I (13) are dissolved in 10 ml of ethanol, 100 mg of Pd/C (10%) are added and the mixture is hydrogenated at room temperature under normal pressure. After the catalyst has been filtered off with suction, the filtrate is concentrated.
Yield: quantitative
$^1$H-NMR(CDCl$_3$): 3.73 ppm (dd, 1H), 4.0 ppm (doublet, 1H), 4.14 ppm (quartet, 1H), 4.28 ppm (doublet, 1H),

(17)
(3-RS,5a-RS,8a-RS)-1-Tert.-butoxycarbonylmethyl-2-oxo-3-amino-perhydrocyclopent[b]azepine (cis-exo)

205 mg of the "cis-exo" azide compound from Example I (14) are hydrogenated analogously to Example I (16).

Yield: 104 mg $^1$H-NMR(CDCl$_3$): 3.65 ppm (multiplet, 2H), 3.82 ppm (doublet, 1H), 4.39 ppm (doublet, 1H)

(18)
(3-RS,5a-SR,8a-RS)-1-Tert.-butoxycarbonylmethyl-2-oxo-3-amino-perhydrocyclopent[b]azepine (trans)

492 mg of the trans-azide compound from Example I (15) are hydrogenated analogously to Example I (16).

Yield: 480 mg, melting point: 70°–74° C.

$^1$H-NMR(CDCl$_3$): 3.85–4.03 ppm (multiplet, 2H), 3.98 ppm (doublet, 1H), 4.18 ppm (doublet, 1H)

(19)
(3-RS,5a-RS,8a-RS)-1-Tert.-butoxycarbonylmethyl-2-oxo-3-[1-(S)-ethoxycarbonyl-3-phenylpropylamino]-perhydrocyclopent[b]azepine (cis-exo)

180 mg of amine from Example I (17) and 67 mg of triethylamine are dissolved in 0.6 ml of dry methylene chloride. 225 mg of ethyl (D)-2-trifluoromethylsulfonyloxy-4-phenyl-butyrate in 0.3 ml of dry methylene chloride are added and the mixture is left to stand at 5° C. for 14 hours. Thereafter, it is washed with water and the methylene chloride phase is dried and concentrated.

Yield: 0.33 g of diastereomeric mixture

(20)
(3-S,5a-S,8a-S)-1-Tert.-butoxycarbonylmethyl-2-oxo-3-[1-(S)-ethoxycarbonyl-3-phenylpropylamino]-perhydrocyclopent[b]azepine (cis-exo)

The diastereomeric mixture from Example I (19) is separated by column chromatography over silica gel with cyclohexane/ethyl acetate 65:35. 2 diastereomers are obtained. The products eluted are first diastereomer I: $[\alpha]_D^{20} = +2.5°$ (methanol) and then diastereomer II: $[\alpha]_D^{20} = -11.1°$ (methanol) Diastereomer I is said to have the (3-R,5a-R,8a-R) configuration and diastereomer II the (3-S,5a-S,8a-S) configuration. The configuration was extrapolated from the biological results of the end product (compounds from Example I (21) and Example II).

(21)
(3S,5a-S,8a-S)-1-Carboxymethyl-2-oxo-3-[1-(S)-ethoxycarbonyl-3-phenylpropylamino]-perhydrocyclopent[b]azepine (cis-exo)

90 mg of diastereomer II from Example I (20) are dissolved in 0.4 ml of trifluoroacetic acid and the solution is left to stand at room temperature for 140 minutes. Thereafter, the trifluoroacetic acid is evaporated off and the residue is evaporated on a rotary evaporator several times with toluene. The residue is taken up in methanol/water and brought to pH 4.2 with an ion exchanger (IRA 93, acetate form). The ion exchanger is filtered off with suction, the solution is evaporated to dryness on a rotary evaporator with toluene and the residue is evaporated again on a rotary evaporator with ethyl acetate and diethyl ether.

Yield: 61 mg; $[\alpha]_D^{20} = -4.0°$ (c=0.5, methanol).

EXAMPLE II
(3-R,5a-R,8a-R)-1-Carbonylmethyl-2-oxo-3-[1-(S)-ethoxycarbonyl-3-phenylpropylamino]-perhydrocyclopent[b]azepine 90 mg of diastereomer I from Example I (20) are reacted analogously to Example I (21).

Yield: 67 mg, melting point: 95°–103° C.; $[\alpha]_D^{20}$: +1.3° (c=0.6, methanol).

EXAMPLE III
(3-S,5a-R,8a-R)-1-Carboxymethyl-2-oxo-3-[1-(S)-ethoxycarbonyl-3-phenylpropylamino]-perhydrocyclopent[b]azepine (cis-endo)

(1)
(3-S,5a-R,8a-R)-1-Tert.-butoxycarbonylmethyl-2-oxo-3-[1-(S)-ethoxycarbonyl-3-phenylpropyl-amino]-perhydrocyclopent[b]azepine 580 mg of amine from Example I (16) are reacted analogously to Example I (19).

Yield: 970 mg of diastereomer mixture which is separated by column chromatography analogously to Example I (20). Diastereomer I is eluted first, followed by diastereomer II.

Diastereomer I: $[\alpha]_D^{20} = -5.8°$ (CHCl$_3$)
Diastereomer II: $[\alpha]_D^{20} = +7.0°$ (CHCl$_3$)

On the basis of the biological data of the end product (compound from Example IV), diastereomer I is said to have the (3-R,5a-S,8a-S) configuration, and on the basis of the biological data of the end product (compound from Example III (2)), diastereomer II is said to have the (3-S,5a-R,8a-R) configuration.

(2)
(3-S,5a-R,8a-R)-1-Carboxymethyl-2-oxo-3-[1-(S)-ethoxycarbonyl-3-phenylpropylamino]-perhydrocyclopent[b]azepine 360 mg of diastereomer II from Example III (1) are reacted analogously to Example I (21).

Yield: 251 mg $[\alpha]_D^{20} = +40.6°$ (methanol)

$^1$H-NMR(CDCl$_3$): 2.7 ppm (triplet, 2H), 3.34 ppm (triplet, 1H), 3.72 ppm (triplet, 1H), 4.05–4.35 ppm (multiplet, 5H),

EXAMPLE IV
(3-R,5a-S,8a-S)-1-Carboxymethyl-2-oxo-3-[1-(S)-ethoxycarbonyl-3-phenylpropylamino]-perhydrocyclopent[b]azepine 370 mg of diastereomer I from Example III (1) are reacted analogously to Example I (21).

Yield: 222 mg $[\alpha]_D^{20} = -7.4°$ (methanol)

$^1$H-NMR(CDCl$_3$): 2.7 ppm (multiplet, 2H), 3.21 ppm (triplet, 1H), 3.6 ppm (triplet, 1H), 3.95–4.25 ppm (multiplet, 5H)

EXAMPLE V
(3-S,5a-R,8a-S)-1-Carboxymethyl-2-oxo-3-[1-(S)-ethoxycarbonyl-3-phenylpropylamino]-perhydrocyclopent[b]azepine (trans)

(1)
(3-S,5a-R,8a-S)-1-Tert.-butyloxycarbonylmethyl-2-oxo-3-[1-(S)-ethoxycarbonyl-3-phenylpropylamino]-perhydrocyclopent[b]azepine (trans)

451 mg of amine from Example I (18) are reacted analogously to Example I (19).

Yield: 811 mg of diastereomeric mixture which is separated by column chromatography analogously to Example I (20). Diastereomer I is eluted first, followed by diastereomer II.

Diastereomer I: $[\alpha]_D^{20} = +0.9°$ (c=0.94, Methanol)

Diastereomer II: $[\alpha]_D^{20} = -22.9°$ (c=0.71, Methanol)

On the basis of the biological data of the end product (compound from Example VI), diastereomer I is said to have the (3-R,5a-S,8a-R) configuration, and on the basis of the biological data of the end product from Example V (2), diastereomer II is said to have the (3-S,5a-R,8a-S) configuration.

(2)

(3-S,5a-R,8a-S)-1-Carboxymethyl-2-oxo-3-[1-(S)-ethoxycarbonyl-3-phenylpropylamino]-perhydrocyclopent[b]azepine (trans)

194 mg of diastereomer II from Example V (1) are reacted analogously to Example I (21).

Yield: 85 mg, $[\alpha]_D^{20} = -8.9°$ (c=0.67, Methanol)

$^1$H-NMR(CDCl$_3$): 2.87 ppm (multiplet, 2H), 3.32 ppm (multiplet, 1H), 3.7–4.0 ppm (multiplet, 2H), 4.05–4.3 ppm (multiplet, incl., quartet, 3H), 4.48 ppm (broad doublet, 1H)

EXAMPLE VI (3-R,5a-S,8a-R)-1-Carboxymethyl-2-oxo-3-[1-(S)-ethoxycarbonyl-3-phenylpropylamino]-perhydrocyclopent[b]azepine (trans)

245 mg of diastereomer I from Example V (1) are reacted analogously to Example I (21).

Yield: 114 mg $[\alpha]_D^{20} = +37.6°$ (c=0.95, Methanol)

$^1$H-NMR(CDCl$_3$): 2.7–2.95 ppm (multiplet, 2H), 3.26 ppm (multiplet, 1H), 3.73–3.86 ppm (multiplet, 2H), 4.08 ppm (multiplet, 1H), 4.22–4.4 ppm (multiplet, 3H)

EXAMPLE VII (3-S,5a-R,8a-S)-1-Carboxymethyl-2-oxo-3-[1-(S)-ethoxycarbonyl-3-cyclohexylpropylamino]-perhydrocyclopent[b]azepine (trans)

(3-S,5a-R,8a-S)-1-Tert.-butoxycarbonylmethyl-2-oxo-3-[1-(S)-ethoxycarbonyl-3-cyclohexylpropylamino]-perhydrocyclopent[b]azepine 200 mg of diastereomer II from Example V (1) are dissolved in 20 ml of methanol, 150 mg of rhodium-on-charcoal (5%) are added and the mixture is hydrogenated under a hydrogen pressure of 50 atmospheres at 100° C. for 20 hours.

Yield: 169 mg $[\alpha]_D^{20} = -28.2°$ (c=1.4, Methanol)

(2)

(3-S,5a-R,8a-S)-1-Carboxymethyl-2-oxo-3-[1-(S)-ethoxycarbonyl-3-cyclohexylpropylamino]-perhydrocyclopent[b]azepine 135 mg of the compound from Example VII (1) are reacted analogously to Example I (21). The hydrochloride is obtained with ethanolic HCl.

Yield: 87 mg $[\alpha]_D^{20} = -17.2°$ (c=0.5, Methanol)

Melting point: 170° (decomposition)

EXAMPLE VIII (3-S,5a-R,8a-R)-1-Carboxymethyl-2-oxo-3-[1-(S)-ethoxycarbonyl-n-butylamino]-perhydrocyclopent[b]azepine (cis-endo)

(1)

(3-S,5a-R,8a-R)-1-Tert.-butoxycarbonylmethyl-2-oxo-3-[1-(S)-ethoxycarbonyl-n-butylamino]-perhydrocyclopent[b]azepine 200 mg of the racemate from Example I (16) are reacted analogously to Example I (19) with the exception that ethyl D-2-trifluoromethylsulfonyloxy-n-pentanecarboxylate is taken instead of ethyl D-2-trifluoromethylsulfonyloxy-4-phenylbutyrate.

Yield: 310 mg of diastereomeric mixture which is separated by column chromatography over silica gel analogously to Example I (20). Diastereomer I is eluted first, followed by diastereomer II.

Diastereomer I probably has the (3-R,5a-S,8a-S) configuration and diastereomer II the (3-S,5a-R,8a-R) configuration, analogously to Example V (1)

m/e=410

(3-S,5a-R,8a-R)-1-Carboxymethyl-2-oxo-3-[1-(S)-ethoxycarbonyl-n-butylamino]-perhydrocyclopent[b]azepine 130 mg of diastereomer II from Example VIII (1) are reacted analogously to Example I (21).

Yield: 90 mg m/e: 354

EXAMPLE IX (3-R,5a-S,8a-S)-1-Carboxymethyl-2-oxo-3-[1-(S)-ethoxycarbonyl-n-butylamino]-perhydrocyclopent[b]azepine (cis-endo)

120 mg of diastereomer I from Example VIII (1) are reacted analogously to Example I (21).

Yield: 85 mg, m/e: 354

EXAMPLE X

If the "cis-exo" compound from Example I (17) or the trans compound from Example I (18) is used instead of the "cis-endo" compound from Example I (16) in Example VIII (1) and the procedure is as described in Example VIII and IX, the compound (3-S,5a-S,8a-S)-1-carboxymethyl-2-oxo-3-[1-(S)-ethoxycarbonyl-n-butylamino]-perhydrocyclopent[b]azepine (cis-exo) and the (3-R,5a-R,8a-R)-diastereomer or the compound (3-S,5a-S,8a-S)-1-carboxymethyl-2-oxo-3-[1-(S)-ethoxycarbonyl-n-butylamino]-perhydrocyclopent[b]azepine and the (3-R,5a-R,8a-R) diastereomer are obtained.

EXAMPLE XI (3-S,5a-R,8a-R)-1-Carboxymethyl-2-oxo-3-[1-(S)-carboxy-3-phenylpropylamino]-perhydrocyclopent[b]azepine (cis-endo)

277 mg of the compound from Example III (2) are suspended in 4.5 ml of water. 0.465 ml of 4N aqueous KOH solution are added and the mixture is left to stand at room temperature for 14 hours. It is filtered and the filtrate is brought to pH 1.5 with concentrated aqueous HCl. The precipitate is filtered off with suction, washed with water and dried over P$_2$O$_5$.

Yield: 223 mg, melting point: 243°–246° C., $[\alpha]_D^{20} = +51.5°$ $^1$H-NMR(DMSO-d$_6$): 2.64 ppm (multiplet, 2H), 3.13 ppm (multiplet, 1H), 3.93 ppm (dd)

EXAMPLE XII (3-S,5a-R,8a-S)-1-Carboxymethyl-2-oxo-3-[1-(S)-carboxy-3-phenylpropylamino]-perhydrocyclopent[b]azepine (trans)

200 mg of the compound from Example V (2) are reacted analogously to Example XI.

Yield: 125 mg, melting point: 209°–211° C., $[\alpha]_D^{20}$: $-11°$ (c=1, Methanol)

$^1$H-NMR(DMSO-d$_6$): 2.7 ppm (multiplet, 2H), 3.03 ppm (multiplet, 1H), 3.48 ppm (doublet, 1H), 3.98 ppm (dd, 2H), 4.72 ppm (multiplet, 1H), m/e: 533 (M+H$^+$+2 TMS) after silylation (TMS=trimethylsilyl)

EXAMPLE XIII (3-S,5a-S,8a-S)-1-Carboxymethyl-2-oxo-3-[1-(S)-carboxy-3-phenylpropylamino]-perhydrocyclopent[b]azepine (cis-exo)

200 mg of the compound from Example I (21) are reacted analogously to Example XI.

Yield: 114 mg m/e: 533 (M+H$^+$+2 TMS) after silylation (TMS=trimethylsilyl)

EXAMPLE XIV (3-S,5a-R,8a-S)-1-Carboxymethyl-2-oxo-3-[1-(S)-carboxy-3-cyclohexylpropylamino]-perhydrocyclopent[b]azepine (trans)

78 mg of the compound from Example VII (2) are reacted analogously to Example XI.

Yield: 40 mg, $[\alpha]_D^{20} = -12.1°$ (c=0.4, Methanol)

m/e: 538 (M+H$^+$+2 TMS) after silylation (TMS=trimethylsilyl)

EXAMPLE XV

Analogously to Example XI, from the compounds from
(a) Example VIII (2)
(b) Example X (3-S-cis-exo diastereomer)
(c) Example X (3-S-trans diastereomer),
the compounds
(a) (3-S,5a-R,8a-R)-1-Carboxymethyl-2-oxo-3-[1-(S)-carboxy-n-butylamino]-perhydrocyclopent[b]azepine
(b) (3-S,5a-S,8a-S)-1-Carboxymethyl-2-oxo-3-[1-(S)-carboxy-n-butylamino]-perhydrocyclopent[b]azepine and
(c) (3-S,5a-R,8a-S)-1-Carboxymethyl-2-oxo-3-[1-(S)-carboxy-n-butylamino]-perhydrocyclopent[b]azepine
are obtained.

EXAMPLE XVI

The corresponding perhydrocyclopent[b]azocine derivatives, such as, for example, (3-S,6a-R,9a-R)-1-carboxymethyl-2-oxo-3-(1-(S)-carboxy-3-phenylpropylamino)-perhydro-2H-cyclopent[b]azocine corresponding to Example I, Example III and Example XI, can be prepared in an analogous manner to Examples I-XV.

We claim:
1. A compound of the formula

(I)

in which
m is 1 or 2,
n is 0, 1 or 2 and
R$^1$ and R$^2$ are identical or different and are hydrogen, (C$_1$–C$_6$)-alkyl or (C$_1$–C$_6$)-alkyl which is monosubstituted by hydroxyl, mercapto, (C$_1$–C$_2$)-alkoxy, (C$_1$–C$_2$)-alkylmercapto, carboxyl, (C$_1$–C$_2$)-alkoxycarbonyl, 3-indolyl, imidazolyl, carbamoyl, amino or guanidino, (C$_2$–C$_6$)-alkenyl, (C$_3$–C$_9$)-cycloalkyl, (C$_3$–C$_9$)-cycloalkenyl, (C$_3$–C$_7$)-cycloalkyl-(C$_1$–C$_4$)-alkyl, (C$_6$–C$_{92}$)-aryl, partly hydrogenated (C$_6$–C$_{12}$)-aryl or (C$_6$–C$_{12}$)-aryl-(C$_1$–C$_4$)-alkyl, which can carry a hydroxyl group in the aryl part,
R$^3$ and R$^4$ are identical or different and are hydrogen, (C$_1$–C$_6$)-alkyl, (C$_2$–C$_6$)-alkenyl or (C$_6$–C$_{12}$)-aryl-(C$_1$–C$_4$)-alkyl, which can be monosubstituted in the aryl part by methoxy or nitro,
Y is hydrogen or hydroxyl,
Z is hydrogen or
Y and Z together are oxygen, and
X is (C$_1$–C$_6$)-alkyl, which can be substituted by one or more of amino, acylamino, (C$_1$–C$_4$)-alkylamino or di-(C$_1$–C$_9$)-alkyamino, or by (C$_2$–C$_6$)-alkenyl, (C$_5$–C$_9$)-cycloalkyl, (C$_6$–C$_{12}$)-aryl, which can be mono-, di- or trisubstituted by one or more of (C$_1$–C$_4$)-alkyl, (C$_1$–C$_4$)-alkoxy, hydroxyl, halogen, nitro, amino, (C$_1$–C$_4$)-alkylamino, di-(C$_1$–C$_4$)-alkylamino or methylenedioxy, or by indol-3-yl, and
(C$_6$–C$_{12}$)-aryl is phenyl, naphthyl or biphenylyl, and in the above-defined radicals R$^1$, R$^2$ and X:
a free phenolic OH group can be optionally protected by benzyloxycarbonyl, 2-bromobenzyloxycarbonyl, benzyl, 4-methoxybenzyl, picolyl or t-butyl;
a free alcoholic OH group can be protected by t-butyl or benzyl;
a free carboxyl group can be protected by methyl, ethyl, benzyl, 4-nitrobenzyl, 4-methoxybenzyl, 4-picolyl, t-butyl or benzoylmethyl;
a free amino group can be protected by t-butoxycarbonyl, benzyloxycarbonyl, 4-picolyl-oxycarbonyl, 9-fluorenylmethoxycarbonyl, 2,2,2-trichloro-t-butoxycarbonyl, a,a-dimethyl-3,5-dimethoxybenzyloxycarbonyl, 4-biphenylyl-dimethylmethoxycarbonyl, 4-nitrobenzyloxycarbonyl, 4-methoxybenzyloxycarbonyl, 1-methyl-cyclobutyloxycarbonyl, isobornyloxycarbonyl, 1-adamantyl-oxycarbonyl or 1-(1-adamantyl-1-methylethoxycarbonyl; and a free guanidino group can be nitrated or can be protected by the protective groups defined above for a free amino group, or a physiologically acceptable salt thereof.

2. A compound of the formula I as claimed in claim 1, in which m is 1 and n is 1, $R^1$ is hydrogen, $(C_1-C_3)$-alkyl, $(C_3-C_6)$-cycloalkyl, $(C_3-C_6)$-cycloalkyl-$(C_1-C_2)$-alkyl or allyl, $R^2$ is hydrogen, $(C_1-C_3)$-alkyl, $(C_3-C_6)$-cycloalkyl, $(C_3-C_6)$-cycloalkyl-$(C_1-C_2)$-alkyl or allyl, $R^3$ is hydrogen, $(C_1-C_4)$-alkyl, benzyl or 4-methoxybenzyl, $R^4$ is hydrogen, $(C_1-C_4)$-alkyl, benzyl or 4-methoxybenzyl, X is phenyl or phenyl which is mono- or disubstituted by fluorine and/or chlorine, methyl, cyclohexyl or aminoethyl, Y denotes hydrogen or hydroxyl, and Z denotes hydrogen, or Y and Z together represent oxygen.

3. A compound of the formula I as claimed in claim 1, in which m=1, n=1, $R^1$, $R^2$ and $R^3$ each denote hydrogen, $R^4$ denotes hydrogen or ethyl, Y and Z each denote hydrogen and X denotes phenyl.

4. A compound of the formula I as claimed in claim 1, in which the chiral carbon atoms labeled with an asterisk (*) have the S configuration.

5. 1-Carboxymethyl-3-(S)-[1-(S)-ethoxycarbonyl-3-phenylpropylamino]-2-oxo-perhydrocyclopent[b]-azepine, 1-Carboxymethyl-3-(S)-[1-(S)-carboxy-3-phenylpropylamino]-2-oxo-perhydrocyclopent[b]azepine, 1-Carboxymethyl-3-(S)-[1-(S)-ethoxycarbonyl-butylamino]-2-oxo-perhydrocyclopent[b]azepine, 1-Carboxymethyl-3-(S)-[1-(S)-carboxy-butylamino]-2-oxo-perhydrocyclopent[b]azepine, 1-Carboxomethyl-3-(S)-[1-(S)-ethoxycarbonyl-5-amino-pentylamino]-2-oxo-perhydrocyclopent[b]azepine, 1-Carboxymethyl-3-(S)-[1-(S)-carboxy-5-amino-pentylamino]-2-oxo-perhydrocyclopent[b]azepine, a stereoisomer thereof or a physiologically acceptable salt thereof.

6. 1-Carboxymethyl-3-(S)-[1-(S)-ethoxycarbonyl-3-phenylpropylamino]-2-oxo-perhydro-2H-cyclopent[b]azocine, 1-Carboxymethyl-3-(S)-[1-(S)-carboxy-3-phenylpropylamino]-2-oxo-perhydro-2H-cyclopent[b]azocine, a stereoisomer thereof or a physiologically acceptable salt thereof.

7. A compound of the formula XIII

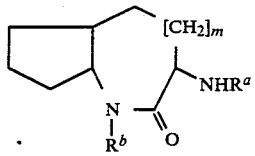 (XIII)

in which m denotes 1 or 2

(a) $R^a$ and $R^b$ each denote hydrogen, (b) $R^a$ denotes hydrogen and $R^b$ represents a radical

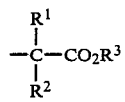

in which $R^1$, $R^2$ and $R^3$ are as defined in claim 1, (c) $R^a$ represents a radical

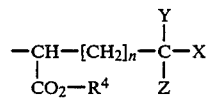

in which n, $R^4$, X, Y and Z are defined above and $R^b$ denotes hydrogen, or (d) $R^a$ represents a radical

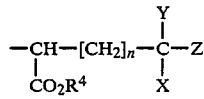

in which n, $R^4$, X, Y and Z are as defined above, and $R^b$ represents a radical

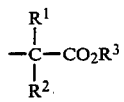

in which $R^1$, $R^2$ and $R^3$ are as defined above.

8. A hypotensive composition comprising an effective amount of a compound as claimed in claim 1 or a physiologically acceptable salt thereof and a physiologically acceptable carrier.

9. A method of treating hypertension which comprises administering of an effective amount of a compound as claimed in claim 1 or a physiologically acceptable salt thereof.

10. A method of treating heart diseases which comprises administering of an effective amount of a compound as claimed in claim 1 or a physiologically acceptable salt thereof.

* * * * *